United States Patent [19]

Aviv et al.

[11] Patent Number: 4,871,835
[45] Date of Patent: Oct. 3, 1989

[54] ANALOGS OF HGH HAVING ANTAGONISTIC ACTIVITY, AND USES THEREOF

[75] Inventors: Haim Aviv; Marian Gorecki, both of Rehovot; Avigdor Levanon, Netania; Amos Oppenheim, Jerusalem; Tikva Vogel, Rehovot; Pinhas E. Zeelon, Hashiva; Menachem Zeevi, Ramat Gan, all of Israel

[73] Assignee: Bio-Technology General Corp., New York, N.Y.

[21] Appl. No.: 691,230

[22] Filed: Jan. 14, 1985

Related U.S. Application Data

[63] Continuation-in-part of Ser. No. 514,188, Jul. 15, 1983.

[51] Int. Cl.[4] .............................................. C07K 13/00
[52] U.S. Cl. .................................... 530/399; 530/350; 530/806; 530/820; 530/808; 435/68; 435/70; 435/172.2; 514/2
[58] Field of Search ............... 530/350, 399, 806, 820, 530/808; 435/68, 70; 514/2

[56] References Cited

U.S. PATENT DOCUMENTS 4,443,539 4/1984 Fraser et al. ......................... 435/68
4,658,021 4/1987 Goeddel et al. ..................... 530/399
4,665,160 5/1987 Seebury .............................. 530/399

FOREIGN PATENT DOCUMENTS 0020147 12/1980 European Pat. Off. .
0121764 10/1984 European Pat. Off. .
WO84/02534 7/1984 PCT Int'l Appl. .
2073245 10/1981 United Kingdom .

OTHER PUBLICATIONS

Seebury, *DNA*, 1982, vol. 1(3), p. 239.

Lewis et al., *Biochem. Biophys. Res. Comm.*, 92(2), 1980, pp. 511–516.
DeGeeter, *CA*, vol. 99, 1983, #157232u.
Russell et al., *JBC*, 256, 1981, pp. 296–300.
Lewis et al., *JBC*, 253(8), 1978, pp. 2679–2687.
Goeddel et al., *Nature*, 281, 1979, pp. 544–548.
Seebury et al., *Nature*, 276, 1978, pp. 795–798.
Ross et al., Hormone Design, 1982, pp. 313–318.
Arieh Gertler et al., Endocrinology, 116(4): 1636–1644 (1985).
Alejandro C. Paladini et al., CRC Critical Reviews in Biochemistry, 15(1): 25–56.

*Primary Examiner*—J. R. Brown
*Assistant Examiner*—Garnette D. Draper
*Attorney, Agent, or Firm*—John P. White

[57] ABSTRACT

Analogs of hGH having the activity of naturally occurring hGH and a similar amino acid sequence varying from the sequence of natural hGh by the addition of one or more amino acids, e.g. methione or methionine-leucine, to the N-terminus of natural hGH have been produced, recovered and purified. Such analogs may be incorporated into pharmaceutical compositions and administered to a subject to increase the level of hGH in the subject.

Analogs of hGH which comprise the amino acid sequence of natural hGH from the N-terminus of which one or more amino acids have been deleted, e.g. Met[14]hGh, have been produced, recovered and purified. Such analogs may be incorporated into pharmaceutical compositions and administered to a subject to lower the level of hGH in the subject.

A plasmid has been constructed which directs the expression of an analog of hGH having the amino acid sequence methionine-leucine added to the N-terminus of natural hGH. This plasmid has been introduced into *Escherichia coli*, the resulting *Escherichia coli* grown and the analog recovered and purified.

3 Claims, No Drawings

ANALOGS OF HGH HAVING ANTAGONISTIC ACTIVITY, AND USES THEREOF

This application is a continuation in part of U.S. Ser. No. 514,188, filed July 15, 1983, the contents of which are hereby incorporated by reference into the present application.

BACKGROUND OF THE INVENTION

One aspect of genetic engineering involves insertion of foreign DNA sequences derived from eukaryotic sources into *Escherichia coli* or other microorganisms. A further refinement concerns inducing the resulting microorganisms to produce polypeptides encoded by the foreign DNA. Production of polypeptides can be considered a two-step process, each step including numerous substeps. The two steps are transcription and translation. To produce a polypeptide efficiently and in quantity both steps must be efficient. Transcription is the production of mRNA from the gene (DNA). Translation is the production of polypeptide from the mRNA.

A critical substep of the transcription process is initiation, i.e., the binding of RNA polymerase to a promoter-operator region. The sequence of deoxyribonucleotide bases which is the promoter region may vary and thereby effect the promoter's relative efficiency which depends on the affinity of the RNA polymerase for the promoter.

The efficiency of translation is affected by mRNA stability. Increased mRNA stability permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known a the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the secondary structure of the mRNA in the region of the Shine-Dalgarno sequence and the AUG codon and the distance between the Shine-Dalgarno sequence and the AUG codon each plate a critical role in determining the efficiency of translation are premature termination and attenuation. Efficiency of translation can be improved by removing the attenuation sites.

A difficulty encountered in attempts to produce high amounts of eukaryotic polypeptides in bacterial cells involves the inability of cells producing large amounts of mRNA to grow efficiently. This difficulty can be eliminated by preventing transcription by a process known as repression. In repression genes are switched off due to the action of protein inhibitor (repressor protein) which prevents transcription by binding to the operator region. After microorganisms have grown to desired cell densities, the repressed genes are activated by destruction of the repressor or by addition of the molecules known as inducers which overcome the effect of the repressor.

Numerous reports may be found in the literature concerning the cloning of eucaryotic genes in plasmids containing the $P_L$ promoter from λ bacteriophage. (Bernard, H. V. et al., Gene (1979) 5, 59; Derom, C. et al., Gene (1982) 17, 45; Gheysen, D. et al., Gene (1982) 17, 55; Hedgpeth, J. et al., Mol. Gen. Genet. (1978) 163, 197; Remaut, E. et al., (1981) Gene 15, 81; and Derynck, R., et al., Nature (1980) 287, 193. In addition, European patent application No. 041.767, published Dec. 16, 1981 describes expression vectors containing the $P_L$ promoter from λ bacteriophage. However, none of these references describe the use of the $C_{II}$ ribosomal binding site.

The use of a vector containing the $P_L$ promoter from λ bacteriophage and the $C_{II}$ ribosomal binding site has been described. (Oppenheim, A. B. et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing $P_L$ from λ bacteriophage, Nut and the $C_{II}$ ribosomal binding site to synthesize a "eucaryotic" polypeptide (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed. The present invention in one embodiment, i.e., pMG100, may have certain similarities to this vector. However, it is not transformed into a host lysogen, but rather into suitable *E. coli* host strains which contain the thermolabile repressor $C_I$ and the N gene but from which the rest of the lysogen has been removed. Moreover, it has been employed to produce bGH and hGH analogs in amounts in excess of 20% to total cell protein.

In addition, in other embodiments of this invention ribosomal binding sites which differ from $C_{II}$ are employed. Also, in the presently most preferred vectors, pND5 and its derivatives, nonessential sequences have been removed to create a vector permitting polypeptide production in amounts which are more than 10% greater than those obtained with pMG100.

Recently, applicants have learned of the existence of a pending M. Rosenberg U.S. patent application Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the $C_{II}$ ribosomal inding region has been altered. (p3, line 27) In the present invention such alteration is possible.

No disclosure is present in the art concerning: successful expression with a $P_L$-$C_{II}$ containing vector system of bovine or human growth hormones; production of bGH or hGH analogs having biological activity; compositions containing such analogs or uses of them; or induction methods for achieving polypeptide production in amounts greater than 20% of the total protein produced by the host.

The only disclosure in the art concerning production of bGH analogs by hosts transformed with genetically engineered vectors involves the use of the Trp promoter to produce a bGH analog having the amino acid Met at the N-terminus of the phenylalanine form of natural bGH (Seeburg, P. H. et al., DNA (1983) 2, 37.

The only disclosure in the art concerning production of hGH analogs by hosts transformed with genetically engineered vectors involves the use of the Lac and Trps promoters to produce an analog of hGH having the amino acid Met at the N-terminus of the natural hGH. (Goedell, D. V. et al., Nature (1979) 281, 544)

SUMMARY OF THE INVENTION

Analogs of hGH having the activity of naturally occurring hGH and a similar amino acid sequence varying from the sequence of natural hGH by the addition of one or more amino acids, e.g. methione or methionineleucine, to the N-terminus of natural hGH have been produced, recovered and purified. Such analogs may be incorporated into pharmaceutical compositions and administered to a subject to increase the level of hGH in the subject.

Analogs of hGH which comprise the amino acid sequence of natural hGH from the N-terminus of which one or more amino acids have been deleted, e.g. Met$^{14}$hGH, have been produced, recovered and purified. Such analogs may be incorporated into pharmaceutical compositions and administered to a subject to lower the level of hGH in the subject.

A plasmid has been constructed which directs the expression of an analog of hGH having the amino acid sequence methionine-leucine added to the N-terminus of natural hGH. This plasmid has been introduced into *Escherichia coli*, the resulting *Escherichia coli* grown and the analog recovered and purified.

DESCRIPTION OF THE FIGURES

FIG. 1 Construction of pMH100 expression vector. This plasmid was built by inserting a fragment of λ phage DNA contained between restriction sites HaeIII (location 38150) and Sau3a (location 38362) into a pKC30 plasmid DNA cleaved with HpaI and BamHl. The HaeIII-Sau3a fragment carries nut$_R$, t$_{R1}$, cy$^-$ and ribosomal binding site of C$_{II}$ protein (C$_{II}$-RBS). Subcloning of the C$_{II}$-RBS containing DNA into pKC30 creates pMG100 which contains a unique BamH1 restriction site right after the ATG initiation codon of C$_{II}$-RBS and an Nde1 restriction site within the ATG triplet (bottom inset). Numbers in parentheses denote location of restriction sites on the λ phage DNA.

FIG. 2. Construction of pRec ⅔ plasmid. A bGH cDNA containing plasmid, D$_4$, was digested with HaeII. A resulting 1600 bp large fragment was purified and subjected to digestion at 37° C. for 5 minutes with 5 units of S1 exonuclease. A synthetic EcoR1 linker with the sequence:

```
GGAATTCC
CCTTAAGG
``` was attached by ligation. The product was cleaved with EcoR1 and inserted into pBR322 which has been cleaved with EcoR1. A clone, pALR1, was isolated which upon cleavage with EcoR1 released a 1200 bp fragment with the sequence:

```
AATTCCCA...
    GGGT...
``` at the 5' end. Formation of this sequence demonstrates that pALR1 contains an EcoR1 restriction site which includes the TTC codon for residue number 1 (phenylalanine) of authentic bGH. pALR1 was subjected to a partial cleavage with Pst1. The digest was ligated with HindIII linkers and cleaved with EcoR1 and HindIII. The fragment containing bGH cDNA was isolated and subcloned into pBR322 between EcoR1 and HindIII restriction sites to give pAL500. The subcloned bGH cDNA fragment was then excised from pAL500 with EcoR1 and HindIII, "filled in" with DNA polymerase "Klenow" fragment and inserted into the pMG100 expression vector (FIG. 1) opened at the BamH1 site and also "filled in" as above. The resulting vector pREC 2/2, expresses a modified bGH which is altered at its amino terminus as follows:

MetAspGlnPhe$^1$Pro$^2$ . . . bGH

The plasmid pREC 2/2 was disgested with Pst1 and the fragment containing the P$_L$ promoter and the 5' end of the bGH gene (designated fragment A) was isolated. This fragment was ligated to a Pst1 fragment from pAL 500 (designated fragment B). The then resulting vector, pRec ⅔, expresses a modified bGH which is altered at its amino terminus as follows:

MetAspGlnPhe$^1$Pro$^2$ . . . bGH

FIG. 3. Construction of expression vectors pND5, pND55 and pRO11. A plasmid pOG7 (A. Oppenheim, S. Gottesman and M. Gottesman, J. Mol. Biol. (1982) 158, 327) was cleaved with Nde1. The ends of the large fragment carrying the P$_L$ promoter nut$_L$, t$_R$ and C$_{II}$-RBS were ligated to give the pND5 expression vector. This pND5 vector DNA is opened with Nde1. Insertion of that Nde1 fragment from pRec ⅔ (FIG. 2) which contains bGH cDNA results in a plasmid pRO11 which appears to be a better expressor of the modified bGH described in FIG. 2 than pRec ⅔. Insertion of synthetic linkers with the sequence:

```
TATGAGCTCA
ACTCGAGTAT
``` into pOG7 cleaved with Nde1 results in a expression vector pND55 which contains a unique Sac1 restriction site in front of ATG. When pND55 is cleaved with Sac1 and treated with DNA polymerase "Klenow" fragment an ATG initiation codon results which follows the P$_L$ promoter and C$_{II}$-RBS. This vector is suitable for expression of a wide variety of eukaryotic genes lacking an ATG initiation codon.

FIG. 4. Construction of pTV 18(1) and pTV 104(2). A plasmid, pTVHGH was prepared by cloning cDNA encoding hGH into the HindIII site of pBR 322 using standard methods. Meth. Enzymol. (1979) 68, 75. This plasmid was digested with HindIII. The resulting 800 base pair fragment was purified and further digested with FnuDII and "filled in" with DNA polymerase "Klenow" fragment. This treatment removes codons for the first 16 amino acids of hGH. The resulting DNA fragment is ligated with a synthetic linker which restores the codons for the sequence of hGH from Met[14] and regenerates an NdeI restriction site in front of the ATG codon for Met[14]. After treatment with NdeI this semisynthetic DNA was inserted into the pND5 vector opened with NdeI. The resulting plasmid pTV 18(1) (formerly designated pTV 1(8)) expresses hGH under control of the $P_L$ promoter. This hGH is an analog missing the first 13 amino acid residues and having at its N-terminus Met[14].

Plasmid pTV 18(1) was partially digested with NdeI and ligated with a synthetic linker which contains the codons for amino acids 1-13 of hGH:

```
TATGTTCCCAACCATTCCATTATCCCGTCTGTTCGACAACGC
  ACAAGGGTTGGTAAGGTAATAGGGCAGACAAGCTGTTGCGAT.
```

The linker is also complementary to the NdeI site on pTV 18(1) and positions the complete hGH gene in phase with the ATG initiation codon of the pND5 expression vector (FIG. 3). Thus, the resulting plasmid, pTV 104(2), expresses native hGH with an extra methionine at the N-terminus.

FIG. 5 shows the vector pAL Trp 46 which contains the Trp promoter and the first seven amino acids of the Trp E gene transcriptionally fused to the β-galactosidase gene.

FIGS. 6, 7 and 8 show a series of expression vectors (Tac) containing a part of the Trp promoter and Lac operator followed by restriction sites for insertion of a desired gene and expression of bGH under the control of Tac promoter.

FIGS. 9 and 10 show expression vectors containing bGH cDNA under the control of the histidine promoter.

FIG. 11 shows insertion of the bGH gene into an expression vector under the control of the Lac promoter.

FIG. 12 shows expression of bGH gene under control of Omp F promoter.

FIG. 13. Construction of Met[4]-bGH analog pAL401 and expression vectors pND6 and pND11 with altered restriction sites: pAL401 which expresses a modified form of bGH which is lacking the first three amino acids at the amino terminus of the bGH (Met[4]bGH) was constructed by triple ligation of the following:
(a) a bGH DNA fragment of 623 base pairs with PvuII and HindIII excised from pAL500.
(b) a linker formed by synthesizing two DNA strands which after purification were annealed to form:

```
CCATATGTCCTTGTCCGGCCTGTTTGCCAACGCTGTGCT
      GCGACACGAGGCCCGAGTCGTGGACGTGGTCGACG
``` which was "filled in" with DNA polymerase "Klenow" fragment and then cleaved with NdeI and PvuII to prepare a 58 base pair fragment which was recovered and purified.
(c) pND11 which was prepared as follows. An expression vector pOG7 was altered by elimination of HindIII and one of the NdeI sites (distant from the ATG initiator codon) to obtain pND6. Then HindIII linkers were introduced into a SalI site to give pND11.

FIG. 14. Construction of authentic bGH modified with methionine at the amino terminus and various analogs of bGH.
(a) Plasmid pAL401 is treated with NdeI. A synthetic DNA linker containing an ATG initiation signal and the code for the first three amino acids at the amino terminus of native bGH is ligated into the NdeI site. The resulting vector pAL601 leads to the expression of native bGH containing an extra methionine residue at the amino terminus.
(b) Using the strategy described in (a) but modifying the structure of the oligodeoxyribonucleotide linker a class of vectors coding for a series of modified bovine growth hormones is constructed. The modified growth hormones start with methionine at the N-terminus and are followed by any of the twenty naturally occurring amino acids in each of positions 1 and 2, and any of the twenty amino acids other than Glu, Gln, Lys, Met or Trp in position.3. Proceeding from position 4 to the COOH-terminus the sequence is identical to that of native bGH.

FIG. 15. Tibia test. This figure shows the comparison between effect of pRec ⅜ bGH analog and authentic bGH on the bone plate growth of hypophysectomized rats. FIG. 16. Construction of pTV 333(31). pTV333(31) (ATCC accession No. 39981) directs the expression of a novel hGH analog having the sequence met-leμ-hGH. pTV333(31) was constructed by adding a synthetic oligonucleotide sequence to the 5' terminus of the Met[14]hGH of pTV18(1). (See FIG. 4). The synthetic oligonucleotide sequence added was:

```
TATGTTGTTCCCAACCATTCCATTATCCAGATTTTTGACAACGC       5'
  ACAACAAGGGTTGGTAAGGTAATAGGTCTGAAAAACTGTTGCGAT
```

FIG. 17. Construction of pTV304(10). pTV304(10) is similar to pTV104(2) in that it directs the expression of Met-hGH.

It differs from pTV104(2) in that the nucleotide sequence at the 5' end of the gene corresponds exactly to that found in the human genome. pTV304(10) was constructed by adding a synthetic oligonucleotide sequence at the 5' end of the hGH gene in the plasmid pTV18(1). (See FIG. 4). The sequence of the synthetic oligonucleotide was:

```
TATGTTCCCAACCATTCCATTATCCAGACTTTTTGACAACGC         5'
   ACAAGGGTTGGTAAGGTAATAGGTCTGAAAAACTGTTGCGAT
```

FIGS. 18-23 set forth results obtained in tests of the activity of hGH analogs produced by pTV18(1) and pTV104(2). The tests are described more fully in Example 9.

DETAILED DESCRIPTION OF THE INVENTION

A vector has been developed which enables the achievement of enhanced levels of gene expression and polypeptide expression. The vector is a double-stranded DNA molecule. Upon introduction into a suitable bacterial host cell containing the thermolabile repressor $C_I$ and increasing the temperature of the host to a temperature at which the repressor is destroyed, the vector renders the host cell capable of effecting expression of a desired gene inserted into the vector and production of polypeptide encoded by the gene.

The vector includes in 5' to 3' order the following:

a DNA sequence which contains the promoter and operator $P_LO_L$ from lambda bacteriophage;

the N utilization site for binding antiterminator N protein produced by the host cell;

a DNA sequence which contains a ribosomal binding site for rendering the mRNA of the desired gene capable of binding the ribosomes within the host cell;

an ATG initiation codon or a DNA sequence which is converted into an ATG initiation codon upon insertion of the desired gene into the vector; and a restriction enzyme site for inserting the desired gene into the vector in phase with the ATG initiation codon.

The vector also includes a DNA sequence which contains an origin of replication from a bacterial plasmid capable of autonomous replication in the host cell and a DNA sequence which contains a gene associated with a selectable or identifiable phenotypic trait which is manifested when the vector is present in the host cell.

The host for use with the vector is *Escherichia coli*. The presently preferred strains are A1637, A1645, A2602 and A1563. A1637 is presently the most preferred strain. It was obtained from C600 by inserting transposon containing tetracycline resistance gene within the galactose operon as well as the lambda system for expression which is close to galactose operon. It has been deposited with the American Type Culture Collection in Rockville, Maryland, U.S.A. containing various plasmids as described more fully hereinafter. All such deposits were made pursuant to the Budapest Treaty on the International Recognition of the Deposit of Microorganisms.

A1645 was obtained from A1637 by selection for Gal+ (ability to ferment galactose) as well as loss of tetracycline resistance. It still contains the lambda expression system but part of the transposon has been removed by selection. Its phenotype is C600 r−m+ gal+ thr− leu− lac Z−(λcI857 Δ H1 ΔBAM N+).

A2602 and A1563 are derived from SA500. Their phenotypes are SA500 his−ilu− gal+ Δ8(λCI857ΔH1-ΔBAM N+ and SA500 his−0 ilu−gal+ Δ8 lac Z×A21 (ΔCI859 int2×is1 nutL3 ΔH1), respectively.

Preferably the vector is a covalently closed circular double-stranded molecule. However, it is not essential that the vector be covalently closed.

The vector achieves its enhanced expression levels after the host cell is heated to a temperature at which the $C_I$ repressor is destroyed. A temperature above about 42° C. is effective for this purpose and since it is desired that unnecessary heat damage to the host cells be avoided to as great an extent as possible, it is generally desirable that the temperature never exceed 42° C. by more than a few degrees.

One important component of the vector is the ribosomal binding site. Suitable sites are $C_{II}$ from lambda bacteriophage having the sequence:

```
TAAGGAAATACTTACAT

ATTCCTTTATGAATGTA;
``` a synthetic oligonucleotide having the sequence:

```
TAAGGAAGTACTTACAT

ATTCCTTCATGAATGTA;
``` and
the major head protein gene of bacteriophage lambda having the sequence:

```
TTTTTTTACGGGATTTTTTTATG

AAAAAAATGCCCTAAAAAAATAC.
```

Another component of the vector is the restriction enzyme site for insertion of desired genes into the vector in phase with the ATG initiation codon. Numerous such sites may be used. The presently preferred sites are BamH1, Sac1 and Nde1.

The vector also includes an origin of replication from a bacterial plasmid capable of autonomous replication in the host cell. Suitable such origins of replication may be obtained from a number of sources. Presently preferred are origins of replication derived from pBR322 or pR1.

A DNA sequence which contains a gene associated with a selectable or identifiable phenotypic trait which is manifested when the vector is present in the host cell is also a component of the vector. Suitable genes include those associated with temperature sensitivity or drug resistance, e.g., resistance to ampicillin, chloramphenicol or tetracycline.

Relative to vectors previously described in the scientific literature, the vectors of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoprotein E; viral protein 1 of foot and mouth disease virus, protein A from *S. aureus*, interleukin III, enzymes, or analogs of any of the preceding. By analog is meant a polypeptide having the same activity as the naturally occurring polypeptide but having one or more different amino acids at the N-terminus of the polypeptide.

The vector may be formed by methods well known to those skilled in the art to which the invention relates. Such methods are described in greater detail in various publications identified herein, the contents of which are hereby incorporated by reference into the present disclosure in order to provide complete information concerning the state of the art.

One presently preferred vector is pMG100 having the restriction map shown in FIG. 1. This vector has had cDNA encoding bovine growth hormone inserted into its BamH1 restriction site. The resulting plasmid is designated pRec ₃/₈ bGH. Its restriction map is shown in FIG. 2. The plasmid pRec ₃/₈ bGH was introduced into *Escherichia coli* strain A1637 using conventional transformation methods. The resulting host vector system has been deposited under ATCC No. 39385.

A second presently preferred vector is pND5 having the restriction map shown in FIG. 3. Bovine growth hormone cDNA has been inserted into its Nde1 restriction site. The resulting plasmid is designated pRO11. Its restriction map is also shown in FIG. 3. The plasmid pRO11 was introduced into *E. coli* strain A1637 via transformation. The host vector system which resulted has been deposited under ATCC No. 39390.

The vector pND5 has also been used to clone human growth hormone. One plasmid designated pTV 18(1) and another designated pTV 104(2) have been created by inserting hGH cDNA into the Nde1 restriction sites. pTV 18(1) is shown in FIG. 4. It has been introduced into *E. coli* strain A1637 via transformation. The resulting host vector system has been deposited under ATCC NO. 39386. pTV 104(2) is shown in FIG. 4. It also has been introduced into *E. coli* strain A1637. The resulting host vector system has been deposited under ATCC No. 39384.

Under the same approach other plasmids may be prepared by inserting into the restriction enzyme site of a vector of the invention a gene encoding a desired polypeptide.

The preceding specific host vector systems involve *E. coli* A1637. However, as previously indicated other strains have been used including A1645, A2606 and A1563. These host vector systems may be used to produce polypeptides such as bovine and human growth hormones. To do so the host vector system is grown under suitable conditions permitting production of the polypeptide which is then recovered.

Suitable conditions involve growth of the host vector system for an appropriate period of time at about 42° C. followed by continued growth at about 37°–39° C. for an additional period of time, the growth being carried out on a suitable medium.

Desirably the initial period of growth is about 10 to 30 minutes at 42° C. followed by growth at 37°–39° C. for a sufficient period of time such that the total period of growth is about 60 to 90 minutes. Preferably the growth is for about 15 minutes at 42° C. followed by about 75 minutes at 38°–39° C. Suitable media include lactalbumin hydrolysate with addition of glucose and brain heart infusion. In order to stably maintain the vector in the host it is critical that the host be maintained under selective pressure, e.g., addition of antibiotic.

By means of the preceding method a number of bGH and hGH analogs has been prepared. These have or may have the activity of the naturally occurring hormones.

bGH analogs have the activity of natural bGH and an identical amino acid sequence except for variations at the N-terminus of up to five (5) amino acids. Examples include the following:

(1) amino acid methionine added to N-terminus of the phenylalanine form of bGH.

(2) amino acid methionine added to N-terminus of the alanine form of bGH.

(3) amino acid sequence Met-Asp-Gln added to N-terminus of the phenylalanine form of bGH.

(4) amino acid sequence Ala-Gly added to N-terminus of the alanine form of bGH.

(5) amino acid sequence Met-Gly added to N-terminus of the alanine form of bGH.

(6) amino acid sequence Met-Asp-Pro-Met-Gly added to N-terminus of the alanine form of bGH.

(7) amino acid sequence Met-Asp-Pro added to N-terminus of the phenylalanine form of bGH.

(8) amino acid sequence Met-Thr-Arg added to N-terminus of the phenylalanine form of bGH.

(9) amino acids up to methionine (4 position) removed from N-terminus of phenylalanine form of bGH.

An analog of bGH having the amino acid sequence:

$$\text{Met-(X)}_n\text{-Y-Met} \ldots$$

wherein Met is the N-terminus, X is any of the twenty naturally occurring amino acids, Y is any of the twenty amino acids other than Glu, Gln, Lys, Met or Trp, n is an integer from 0 to 6 and Met . . . is the sequence of natural bGH from position 4 to the COOH-terminus (position 191).

hGH analogs have the activity of natural hGH and an identical amino acid sequence except for variations at the N-terminus. Examples include the following:

(1) amino acid methionine added to N-terminus of natural hGH.

(2) amino acid sequence methionine-leucine added to the N-terminus of natural hGh.

Each of these variations involve the addition of one or more amino acids to the N-terminus of natural hGH.

In addition, this invention provides antagonists of hGH activity which comprise the amino acid sequence of natural hGH from which one or more amino acids have been deleted.

One such analog of hGH has the amino acid sequence:

$$\text{Met-(X)}_n\text{-Y-Met} \ldots$$

wherein Met is the N-terminus, X is any of the twenty naturally occurring amino acids, Y is any of the twenty amino acids other than Glu, Gln, Lys, Met or Trp, n is an integer from 0 to 13 and Met . . . is the sequence of natural hGH from position 14 to the COOH-terminus (position 191).

Another such analog has the amino acid sequence of natural hGH from which the first thirteen amino acids have been removed to yield methione (14 position) at the N-terminus followed by amino acids 15–191 of natural hGH.

Pharmaceutical compositions may be prepared which contain effective amounts of one or more hGH analog having hGH activity and a suitable carrier. Such carriers are well-known to those skilled in the art. The analogs may be administered directly or in the form of a composition to a human subject, e.g., one afflicted by dwarfism, to treat deficiencies in hGH production by the subject.

Similarly, pharmaceutical compositions may be prepared which contain effective amounts of one or more hGH analog having antagonistic hGH activity and a suitable carrier. Such carriers are well known to those skilled in the art. The analogs may be administered directly or in the form of a composition to a human subject, e.g. one producing excess hGH, to treat or reduce such excess hGH production by the subject.

EXAMPLES

The examples which follow are set forth to aid in understanding the invention by are not intended to, and should not be so construed as to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those skilled in the art and are described in numerous publications including the following:

Principles of Gene Manipulation, An Introduction to Genetic Engineering, 2nd Edition, edited by R. W. Old and S. B. Primrose, University of California Press (1981).

Met. Enzymol. Vol. 68, Recombinant DNA, edited by Ray Wu.

Met. Enzymol. Vol. 65, Nucleic Acids (Part 1), edited by Lawrence Grossman and Kivie Moldave.

T. Maniatis, E. F. Fritsch and J. Sambrook, Molecular Cloning; A Laboratory Manual, Cold Spring Harbor Laboratory, NY (1982).

H. V. Bernard et al., Gene (1979) 5, 59.

A. B. Oppenheim et al., J. Mol. Biol. (1982) 158, 327.

E. Remaut et al., Gene (1981) 15, 81.

EXAMPLE 1

EXPRESSION VECTORS

As used herein the term expression vector refers to a group of plasmids useful for expressing desired genes in bacteria, particularly in E. coli. The desired gene may be inserted into the expression vector or alternatively, the promoters on the expression vector may be excised and placed in front of the desired gene.

I. $P_l$ Expression Vectors

A. pMG 100 pMG 100, as shown in FIG. 1 and described in detail under Description of the Figures is composed of λ DNA inserted into a multicopy plasmid pBR322. The salient features of the λ DNA is that it contains the λ $P_L$ promoter, N utilization sites L and R ($nut_L$ and $nut_R$) termination R1 site ($t_{R1}$), the $C_{II}$ ribosomal binding site and an ATG initiation codon. Other features are shown in FIG. 1.

pMG100 was prepared form pKC30. pKC30 in turn was prepared by subcloning of λ $P_L$ promoter in the following manner.

λ phage DNA was digested with Xho1 and Sma1 restriction endonucleases and the unique fragment comprised of 6393 base pairs was purified and subsequently digested with HindIII and BamH1 restriction endonucleases. The resulting fragment comprised of 2397 base pairs and containing $P_L$ promoter was purified and ligated into a pBR322 DNA large fragment isolated from the HindIII and BamH1 digest. The subclone was identified by colony hybridization, recovered and plasmid DNA isolated (Oppenheim, A. et al., J.Mol.Biol. (1982). 158, 327).

This plasmid and its derivatives containing eukaryotic genes may be maintained in suitable E. coli hosts. The most important feature of the host is that it provides the thermosensitive repressor CI857 and the antitermination N protein. (Gottesman, M. E. et al., J.Mol.Biol. (1978) 140, 197).

This vector has numerous advantages over previously described expression vectors including:

1. Extremely High Levels of Expression: This vector is capable of directing expression of foreign proteins in E. coli at levels as high as 15–25% of the total cellular protein.

2. Thermoinducible Regulation of Expression: The $P_L$ promoter is inactive when the CI repressor is bound to it. The CI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:
(a) a foreign protein which is toxic to E. coli can be produced when desired thus avoiding cell death early in the fermentation process.
(b) overproduction of a protein may stabilize it and prevent proteolytic degradation. (Cheng, Y. E. et al., Gene (1981) 14, 121) Thus, "instantaneous" overproduction using a tightly regulated promoter such as $P_L$ may be preferable to continuous low level production.

3. High Copy Number: The $P_L$ promoter in pMG100 is found on a plasmid with a high copy number in distinction to λ itself which is present in low copy numbers in E. coli. This increases expression levels.

4. Ribosome Binding Site and Initiation Codon: This expression vector contains a strong procaryotic ribosomal binding site (RBS) as well as a translation initiation codon (ATG). Thus, any eukaryotic gene may be cloned without the need for adding an initiation codon. Furthermore, the efficient RBS increases levels of expression.

5. Convenient Restriction Site: The expression vector has a BamHI site located directly following the ATG initiation codon which permits proper positioning of the desired gene in order to achieve optimal expression.

6. Nut Site; N protein which is provided by the host binds to Nut site on the expression vector and thereby prevents termination of transcription at the $t_{R1}$ site.

B. pND5

As shown in Fig. 3, pND5 contains the $P_L$ promoter and the other important components of the expression vectors of this invention. It includes a unique Nde1 site immediately after the ribosomal binding site. The ribosomal binding site differs from the normal $C_{II}$ site. It has the sequence:

TAAGGAAGTACTTACAT

ATTCCTTCATGAATGTA

It may be derived from a mutant or may be chemically synthesized. As described in detail under Description of the Figures pND5 was derived from pOG7. (Oppenheim, A., et. al., J.Mol.Biol. (1982) 158, 327) This vector does not contain a translation initiation codon. It appears to provide superior expression of modified bGH and hGH, particularly enhanced yield relative to pMG100 containing a bGH analog.

C. pND55 pND55 is a derivative of pND5 which contains the convenient restriction site Sac1 in front of $C_{II}$-RBS and ATG initiation codon. Cleavage of the plasmid at this site and subsequent treatment with DNA polymerase Klenow fragment allows one to obtain an ATG initiation codon to which any desired gene can be ligated. (FIG. 3 and Description of FIG. 3.)

II. Trp Expression Vectors

A. pAL Trp 46 pAL Trp 46 contains the Trp promoter and the first seven amino acids of the Trp E gene fused to the β-galactosidase gene. (FIG. 5). The desired gene can be inserted into a BamHI site which follows the 7 amino acids of Trp E.

B. pAL Trp 47; Trp 46 Deleted of Attenuator

This is a construction based on Trp 46 in which the attenuator region of the Trp promoter has been deleted.

C. Trp-Lac Fusions

The construction of this promoter, found on plasmid p4754 is illustrated in FIGS. 6 and 7. A variation of this construction is outlined in FIG. 8.

III. Histidine Promoter Expression Vectors

The construction of this expression vector is illustrated in FIGS. 9 and 10.

IV. Other Promoters Used

A. Lac

This promoter was used in the construction of pYL 301 as shown in FIG. 11.

B. Omp F

This is a promoter system which expresses a protein attached to a signal sequence. The signal sequence is removed when the protein is translocated across the membrane. (FIG. 12)

EXAMPLE 2

Bovine Growth Hormone

The starting point for bGH cDNA modifications is plasmid $D_4$ which has been described previously. (Keshet, E. et al, Nucleic Acids Research (1981) 9, 19). The $D_4$ plasmid is also described in pending U.S. patent application, Ser. No. 245,943, filed Mar. 20, 1981, claiming priority of Israel patent application, Ser. No. 59,690 filed Mar. 24, 1980. It has previously been deposited with the American Type Culture Collection in an *E. coli* host under ATCC No. 31826.

I. pRec ⅔ bGH

The construction of pRec ⅔ is shown in FIG. 2 and described in the Description of the Figures. bGH cDNA from $D_4$ has been manipulated prior to insertion into PMG100 to provide the correct reading frame.

pRec ⅔ has been introduced into various *E. coli* strains including A1637 by transformation using known methods. A1637 containing pRec ⅔ has been deposited under ATCC No. 39385. This strain produces upon growth and induction an analog of bGH having the amino acid sequence Met-Asp-Gln added to the N-terminus of the phenylalanine form of natural bGH. The amount of bGH analog produced by pRec ⅔ was about 23% of the total protein produced by the bacteria as calculated from scanning of Coomasie stained SDS polyacrylamide gels.

pRO11

The construction of pRO11 is shown in FIG. 3 and described in the Description of the Figures. The pND5 vector DNA is restricted with NdeI. Insertion of the NdeI fragment from pRec ⅔ (FIG. 2) which contains bGH cDNA results in the plasmid pRO11.

pRO11 has been introduced into *E. coli* A1637 by transformation. The resulting host vector system has been deposited under ATCC No. 39390. This strain was grown and induced produces the same analog as pRec ⅔. Preliminary results indicate that pRO11 produces up to 20% more bGH analog than pRec ⅔. The methods used to grow the strain, recover the bGH analog produced and purify it are the same as those described for pRec ⅔ in Example 4.

III. pAL401

The construction of pAL401 is shown in FIG. 13 and described in the Description of the Figures. bGH cDNA from $D_4$ by way of pAL-500 (FIG. 2) was inserted into pND11 as shown in FIG. 13.

pAL401 may be introduced into *E. coli* A1637 by transformation. The resulting strain produces an analog of bGH in which $Met^4$ of natural bGH is at the N-terminus and the amino acids preceding $Met^4$ have been deleted.

IV. pAL601

The construction of pAL601 is shown in FIG. 14 and described in the Description of the Figures. It is a derivative of pAL401 (FIG. 13).

pAL601 may be introduced into *E. coli* A1637 by transformation. The resulting strain produces an analog of bGH in which Met has been added to the N-terminus of the phenylalanine form of bGH.

EXAMPLE 3

Human Growth Hormone

The starting point for hGH cDNA was cloning of the cDNA from mRNA purified from hypophyses tumor from acromegalic patients into the HindIII site of pBR322.

I. pTV 18(1)

The construction of PTV 18(1) is shown in FIG. 4 and described in the Description of the Figures. hGH cDNA was manipulated prior to insertion into pND5 to provide the correct reading frame.

pTV 18(1) was introduced into *E. coli* A1637 by transformation. The resulting bacteria have been deposited under ATCC No. 39386. This strain upon growth and induction produces an analog of hGH having the sequence of natural hGH beginning with $Met^{14}$ and lacking amino acids 1–13. The amount of hGH analog produced by pTV 18(1) was about 8% of the total protein produced by the bacteria.

II. pTV 104(2)

The construction of pTV 104(2) is shown in FIG. 4 and described in the Description of the Figures. hGH cDNA was manipulated prior to insertion into pND5 to provide the correct reading frame.

pTV 104(2) was introduced into *E. coli* A1637 by transformation. The resulting bacteria have been deposited under ATCC No. 39384. This strain upon growth and induction produces an analog of hGH having the sequence of natural hGH preceded by Met at the N-terminus. The amount of hGH analog produced by pTV 104(2) was above 25% of the total protein produced by the bacteria.

EXAMPLE 4

Growth of pRec ⅔

Stock Cultures: Stock cultures of pRec ⅔ in A1637 are grown on BHI medium (see inoculum), then diluted twofold with 87% glycerol containing phosphate citrate buffer, and stored at −70° C.

Inoculum: Inoculum is propagated in BHI medium (37 g/l) brain heart infusion (DIFCO). Sterile medium in shake flask is inoculated from stock culture and incubated 15 hours on shaker at 30° C., 200 r.p.m. Subsequent stages in inoculum propagation are carried out in stirred aerated fermentors. Sterile medium is inoculated with 0.2 ml flask culture per l, and incubated 15 hours at 30° C., pH 7±0.5 with agitation and aeration to maintain dissolved oxygen level above 20% air saturation.

Production: Production medium contains:

| Lactalbumin hydrolysate (enzymatic) | 20 g/l |
|---|---|
| Yeast extract | 10 g/l |
| $K_2HPO_4$ | 2.5 g/l |
| NaCl | 10 g/l |
| Ampicillin | 0.1 g/l |
| Biotin | 0.1 mg/l |
| Thiamine | 1 mg/l |
| Trace elements solution | 3 ml/l |

Ampicillin, biotin and thiamine in solution are filter sterilized separately and added to the sterile production medium before inoculation. Sterile glucose solution is added initially to supply 10 g/l, and during the induction and expression procedure to maintain glucose above 10 g/l Trace elements solution contains:

| $MgSO_4 \cdot 7H_2O$ | 170 g/l |
|---|---|
| $FeCl_3$ | 16 g/l |
| $ZnCl_2 \cdot 4H_2O$ | 2 g/l |
| $CoCl_2 \cdot 6H_2O$ | 2 g/l |
| $Na_2MoO_4 \cdot 2H_2O$ | 2 g/l |
| $CaCl_2 \cdot 2H_2O$ | 1 g/l |
| $CuCl_2$ | 1 g/l |
| $H_3BO_3$ | 0.5 g/l |
| Conc. HCl | 100 ml/l |

The medium is inoculated with 5–10% inoculum culture and incubated at 30° C. Agitation-aeration rates are set to maintain dissolved oxygen level above 20% air saturation. The pH is maintained at 7±0.2 with $NH_3$. Once cell concentration reaches about 3 g/l ($OD_{660}=10$) induction is started.

Temperature is raised to 42° C. Maintained there for 15 minutes, then lowered to 38° C. Following incubation at 38° C. for 1–1½ hours, the culture is chilled, and cells are recovered by centrifugation for hormone purification.

Recovery of bGH

One kilogram of bacterial cells is suspended in 10 volumes of the solution containing 50 mM Tris-Cl (pH 7.4), 50 mM EDTA and 25% sucrose in a Warring blender, with a control of blender's speed to minimize foaming. The homogeneous suspension is continuously passed through a Dynomill cell disruptor (Willy A. Bachofen, Basel) and the homogeneous suspension of disrupted cells is clarified first by centrifugation in a Sharpless centrifuge followed by a continuous centrifugation at 20,000 rpm in a Sorvall centrifuge. The precipitate from both centrifugation steps is collected, washed with 50 mM Tris-Cl (pH 7.4) and resuspended in 500 ml of the same buffer. Lysozyme is added to a final concentration of 2 mg/ml and the suspension is incubated for 1 hour at 37° C. Triton X-100 is then added to a final concentration of 1%, the suspension is cooled to 4° C. and centrifuged at 20,000 rpm for 20 minutes in a Sorvall SS34 rotor. The precipitate is collected, washed twice with 50 mM Tris-Cl, resuspended in 500 ml of 50 mM Tris-Cl (pH 7.4), 5 mM $MgCl_2$ and deoxyribonuclease is added to a final concentration of 20 μg/ml. After incubation for 30 minutes at room temperature the precipitate is collected as above, washed twice with 500 ml of 20 mM Tris-Cl (pH 7.4), 100 mM NaCl and 10 mM EDTA, followed by two washings with 500 ml of distilled water. The precipitate is collected by centrifugation and can be stored at −20° C. for an indefinite time. At this stage the bGH is 80% pure as judged by sodium dodecyl sulfate-gel electrophoresis. The yield is approximately 15 g of bGH.

Purification of bGH

One hundred gr of precipitate is suspended in 40 ml distilled water and solubilized by titration with 0.5M NaOH, pH 11.8. The solution is then sonicated for 2 minutes and clarified by centrifugation at 20,000 rpm in a Sorvall SS34 rotor for 20 minutes. The solution is then applied onto a Sepharose CL-6B column (5×100 cm) equilibrated with 6.5 mM borate buffer, pH 11.8. Column is developed at the rate of 100 ml/hr and fractions of 12 ml are collected. The first peak off the column is discarded. The following two peaks are separated and pooled. The first represents aggregated bGH with low activity; the second bGH with high A DEAE-Sephacel (25 g/100 gr. equiv. ppt) column is equilibrated with 6.5 mM borate buffer, pH 9.0. The second bGH peak is brought to pH 9.0 with HCl loaded on the DEAE Sephacel column at a rate of 250 ml/hr. The column is washed with 7.5 ml of 6.5 mM borate buffer, pH 9.0, eluted with 6.5 mM borate buffer, pH 9.0 containing 75 mM NaCl. The fractions with $OD_{280}$ above 0.3 are pooled, dialysed against $H_2O$ in Millipore Pellicon dialysis apparatus and then lyophilized.

EXAMPLE 5

Activity of bGH Analog Produced by pRec 2/3

1. Radioimmunoassay comparison of bGH analog with natural bGH

A solution containing 100 ng/ml bGH analog was prepared in phosphate buffered saline (1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural bGH.

2. Radioreceptor binding Assay

A radioreceptor binding assay was performed with rabbit liver membranes as described by T. Tushima and H. G. Freisen (Y. Chin., Endocr. Metab. (1973) 37, 334 using [125]I-hGH as the tracer and authentic bGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained [125]I-hGH (20,000 cpm of preparation of 30–60 μci/μg), 150–250 μg liver membrane protein and either natural bGH (1–100 ng) or extracts of bacterial bGH. The result demonstrated that the bGH activity of the bGH analog is comparable to that of natural bGH.

3. Tibia Test

The bioactivity of the pRec ⅜ bGH analog recovered from engineering bacterial cells according to Example 4 was evaluated by a tibia test. (Parlow, A. F., et al., Endocrinology (1965) 77, 1126.) Rats were hypophysectomized at 28–30 days of age, then kept for 10–14 days without treatment. Bovine growth hormone derived from bovine pituitaries or from recombinant *E. coli* was dissolved in 0.15M NaCl=0.01M borate, pH 10.0. Rats (4–7 per group) received daily subcutaneous injections of bGH solutions (5–125 μg/day in 0.2 cc) for 5 days while kept on a normal diet (Purina Rat-Chow and water ad-libitum). The animals were sacrificed on the 6th day, their foreleg knee-bones taken out, cut longitudinally, fixed with acetone and stained with 2% AgNO$_3$. The width of the epiphyseal plates were measured by observation through a dissecting binocular (Nikon). Mean values (of 40 readings per rat) were used for the construction of log dose-response curves. Results are shown in FIG. 15.

EXAMPLE 6 bGH Analogs

Table I sets forth a series of plasmids which have been constructed and the analogs which were produced from them.

TABLE I

| PLASMID | AMINO TERMINUS OF bGH ANALOGS |
|---|---|
| Rec ⅜ | Met Asp Gln Phe$^2$ |
| pB 1 | Met Asp Pro Met Gly Ala Phe$^2$ |
| pM 4 | Met Asp Pro Phe$^2$ |
| pM 1 | Met Ala$^1$ Phe$^2$ |
| pM 2 | Met Ala$^1$ Phe$^2$ |
| pAL 401 | Met$^4$ |
| pYL 301 | Met Gly Ala$^1$ Phe$^2$ |
| pAL 302 | 11 A.A + Ala$^1$ Phe$^2$ |
| pHis 129 | Met Thr Arg Phe$^2$ |
| pAL 312 | Met Gly Ala$^1$ Phe$^2$ |
| pAL 322 | Met Gly Ala$^1$ Phe$^2$ |
| pAL 601R | Met Gly Ala$^1$ Phe$^2$ |
| p 18 | Met Gly Ala$^1$ Phe$^2$ |
| PBTG-800 | Met Glu Phe$^2$ |
| pORF 2-12 | Ala Gly Ala$^1$ Phe$^2$ |

EXAMPLE 7

Effect of pRec ⅜ bGH analog on Lactogenesis in Dairy Cows

The lactogenic effect of bGH has been well documented in the scientific literature in the reports of Bines, J. et al, Brit J. Nutri. (1980) 43, 179 and Peel, C. et al, J. Nutr. (1981) 111, 1662. Bauman, D. et al, J. Dairy Sci. Vol. Supp. 1, Abst 86 (1982) reported that milk production was increased by rDNA bGH. An experiment was conducted to determine the effects of pRec ⅜ bGH on lactogenesis in comparison with natural bGH. Eighteen Holstein cows ranging from 141 to 154 days postpartum were randomly assigned to treatment and blocked according to milk production according to the following design.

| Pretreatment | Treatment | Daily GH Injection |
|---|---|---|
| Control | 5 days | Saline |
| Natural bGH | 5 days | 25 mg/day for 10 days |
| pRec ⅜ bGH | 5 days | 25 mg/day for 10 days |

The bGHs were put in solution with 0.1M NaHCO$_3$ aqueous buffer (pH=8.2) at the concentration of 1 mg/ml immediately prior to each day's injections. The cows were injected with placebo or bGH solution daily for 10 days in a subcutaneous site in the neck region. No injections were given during the 5-day pretreatment period.

The cows were milked twice daily at approximately 6:00 a.m. and 5:00 p.m. Milk weights were recorded by the Boumatic system and recorded in the dairy data system.

The average milk production values for the pretreatment and bGH treatment periods are shown in Table II. The production level of the control cows was unchanged while the milk volume increased to a similar degree in both the bGH groups. The natural bGH caused an 11.9% increase in milk for a 10-day period and bGH analog treatment resulted in a 10.2% increase. The data were not analyzed for statistical significance due to the small number of animals, however, the magnitudes of the increases are similar to those reported in the literature.

It was concluded that pRec ⅜bGH stimulates lactogenesis in dairy cows similar to natural bGH.

TABLE II

Bovine Growth Hormone Effect on Lactogenesis
Natural bGH vs pRec ⅜ bGH

| | | Av. Daily Milk Production lb/day | | |
|---|---|---|---|---|
| Treatment Group | No. | Pretreatment 5 days | During GH 10 days | % Increase Over Pretreatment |
| Control | 6 | 57.23 | 57.26 | — |
| Natural bGH 25 mg/day | 5 | 58.54 | 65.50 | 11.9 |
| pRec ⅜ bGH 25 mg/day | 6 | 57.48 | 63.34 | 10.2 |

Each cow was injected daily subcutaneously will either placebo or bGH solution once daily for 10 days.

EXAMPLE 8

Human Growth Hormone Analog

The construction of pTV333(31) (ATCC accession No. 39981) is shown in FIG. 16 and described in the Description of the Figures. The intermediate plasmids in the construction of pTV333(31) are shown in FIG. 4 and described in the Description of the Figures.

pTV333(31) was introduced into *E. coli* strain A2097 by transformation. This strain produces upon growth and induction an analog of human growth hormone (hGH) having the amino acid sequence Met-Leu added to the N-terminal amino acid phenylalanine of natural hGH. The amount of hGH analog produced by this strain was about 6% of the total protein produced by the bacteria as calculated by scanning the hGH band on Coomassie blue stained SDS polyacrylamide gels and determining the total protein by the method of Lowry.

Growth of pTV333(31)

I. Stock Cultures

Stock cultures of pTV333(31) were grown on casein medium (see Inoculum), then diluted two-fold with freezing medium and stored at −80° C. Freezing medium contains per 500 ml:

| | |
|---|---|
| K$_2$HPO$_4$ | 6.3 g |
| KH$_2$PO$_4$ | 1.8 g |
| Na Citrate | 0.45 g |
| MgSO$_4$·7H$_2$O | 0.09 g |
| (NH$_4$)$_2$SO$_4$ | 0.9 g |
| Glycerol | 44.0 g |

II. Inoculum

The inoculum was propagated in 20 g/l Tryptone 10, g/l yeast extract and 2 NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2–10% inoculum and incubated 15 hours at 30° C., pH 7±0.5 with agitation and aeration to maintain a dissolved oxygen level above 20% air saturation.

III. Production

The production medium contains:

| | |
|---|---|
| Tryptone | 20 g/l |
| yeast extract | 10 g/l |
| K$_2$HPO$_4$ | 2.5 g/l |
| MgSO$_4$·7H$_2$O | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine and ampicillin in concentrated solution were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| FeCl$_3$ | 16 g/l |
| ZnCl$_2$·4H$_2$O | 2 g/l |
| CoCl$_2$·6H$_2$O | 2 g/l |
| Na$_2$MoO$_4$·2H$_2$O | 2 g/l |
| CaCl$_2$·2H$_2$O | 1 g/l |
| CuCl$_2$ | 1 g/l |
| H$_3$BO$_3$ | 0.5 g/l |
| Conc. HCl | 100 ml/l |

The medium is inoculated with 0.5–10% inoculum culture and incubated at 30° C. Agitation-aeration rates are set to maintain a dissolved oxygen level above 20% air saturation. The pH is maintained at 7±0.2 with NH$_3$. Once cell concentration reaches about 3.5 g/l (OD$_{660}$=10) induction is started.

The temperature is raised to 42° C. and maintained at 42° C. for 1–5 hours. The culture is then chilled and cells are recovered by centrifugation for hormone purification.

EXAMPLE 9

Activity of hGH Analogs Produced by pTV18(1) and pTV104(2)

I. Radioimmunoassay comparison of hGH analogs with natural hGH

Solutions containing 1000 ng/ml hGH analogs were prepared in phosphate buffered saline (1% BSA). These solutions were diluted serially to concentrations shown in FIG. 18. Duplicate 0.1 ml aliquots of these solutions were submitted to RIA using a double antibody procedure. The dilution curves are shown in FIG. 18.

II. Radioreceptor binding assay

A radioreceptor binding assay was performed with rabbit liver membranes as described by T. Tushima and H. G. Freisen [Y. Chin., Endocr. Meta. (1973) 37, 334] using $^{125}$I-hGH as the tracer and authentic hGH solutions for the construction of calibration curves. Samples were incubated in triplicate for two hours at room temperature 0.3 ml of assay buffer 50 mM Tris, 15 mM Cacl$_2$ and 5 mg/ml in bovine serum albumin, pH 7.6). The tubes contained $^{125}$hGH (20,000 cpm of preparation of 30–60 μci/ug), 150–250 ug liver membrane protein and either natural hGH (1–1,000 ng) or extracts of bacterial hGH analogs. The results shown in FIG. 19 demonstrated that the hGH activity of the Met-hGH analog is comparable to that of natural hGH.

III. Tibia and Weight gain test

The bioactivity of the hGH analogs recovered from genetically engineered bacterial cells was evaluated by a tibia test. [Parlow, A. F., et al., Endocrinology (1965) 77, 1126]. Rats were hypophysectomized at 28–30 days of age, then kept for 10–14 days without treatment. Human growth hormone analogs derived from recombinant *Escherichia coli* was dissolved in 0.15M NaCl=0.01M borate, pH 10.0. Rats (4–7 per group) received daily subcutaneous injections of bGH solutions in 0.2 cc for five days while kept on a normal diets (Purina Rat Chow and water ad-libitum).

The rats were weighed at the start of the experiment and before being sacrificed. FIGS. 20 and 21 show the increases in total body weight as a function of the growth hormone concentration in the daily injection.

The animals were sacrificed on the sixth day, their foreleg knee bones taken out, cut longitudinally, fixed with acetone and stained with 2% AgNO$_3$. The width of the epiphyseal plates were measured by observation through a dissecting binocular (Nikon). Mean values (of 40 readings per rat) were used for the construction of log dose-response curves. Results are shown in FIGS. 22 and 23.

Purification of hGH Analogs

One hundred g of precipitate is suspended in 40 ml distilled water and solubilized by titration with 0.5M NaOH to pH 10.0. The solution was centrifuged (20,000 rpm in a Sorvall SS34 rotor for 20 minutes.) The supernatant was further titrated to pH 11.5 and then sonicated for two minutes and clarified by centrifugation at 20,000 rpm in Sorvall SS34 rotor for 20 minutes. The solution is then applied onto a Sepharose CL-6B column (5×100 cm) equilibratd with 6.5 mM borate buffer, pH 11.5. The column is developed at the rate of 100 ml/hr and fractions of 12 ml are collected. The first peak off the column is discarded. The following two peaks are separated and pooled. The first represents aggregated hGH with low activity; the second hGH with high activity.

A DEAE-Sephacel (25 g/100 g equiv. ppt) column is equilibrated with 6.5 mM borate buffer, pH 9.8. The second hGH peak is brought to pH 9.8 with HCl loaded on the DEAE Sephacel column at a rate of 250 ml/hr. The Column is washed with 7.5 ml of 6.5 mM borate buffer, pH 9.8 containing 100 mM NaCl. The fractions with OD$_{280}$ above 0.3 are pooled, dialysed against H$_2$O in Millipore Pellicon dialysis apparatus and then lyophilized.

EXAMPLE 10

Activity of hGH Analog Produced by pTV18(1)

Lactogenic properties of human growth hormone were described over 20 years ago (1) and were confirmed in several species including mice (2) parimates (3) and cows (4). One of the most specific, accurate and sensitive bioassays for lactogenic hormones is based on its mitogenic effect on NB2 rat lymphoma cells. These cells are absolutely dependent on PRL, hGH or other lactogenic hormones for their proliferation when cultured in 10% horse serum supplemented medium (5–7). This assay therefore was chosen to study the in vitro effect of the new 20K derivative of hGH (Met$^{14}$hGH, 14–191) obtained by recombinant DNA technology. An additional bioassay used in the present study was the stimulation of fat synthesis in explants from bovine lactating mammary tissue which was found (4) to be highly dependent upon the presence of bPRL, oPRL or hGH.

Materials and Methods

Materials

Human growth hormone (hGH-83-8-29 H 2.2 IU/mg) was prepared in our laboratory; Ovine PRL (oPRL; (oPRL; NIH-P-S12, 35 IU/mg) and bovine PRL (bPRL, 86) were obtained from the Hormone Distribution Program, National Institutes of Health, Department of Health and Human Services, U.S.A. Radioiodinated hGH ([$^{125}$I]-hGH) was prepared as described earlier (8, 9). Carrier-free Na[$^{125}$I] and CH$_3$[$^{14}$]CHOOH (56 mCi/mmole) were purchased from New England Nuclear Corp. (Boston, MA, U.S.A.). Monoclonal antibodies against hGH were prepared (10). Human growth hormone analog lacking 13 amino acids at the amino terminus, beginning with the amino acid methionine which is naturally located at residue no. 14 (Met$^{14}$hGH) was produced in the efficient host-vector system described herein which expressed this polypeptide at a level of more than 15% of total bacterial protein. Gram quantities of the hormone were purified to a high degree (generally 80% purity). 15% NaDodSO$_4$/polyacrylamide gel electrophoresis in presence of $\beta$-mercaptoethanol gave an expected 20K dalton band, and analytical isoelectrofocusing revealed that the isoelectric point is close to that of native hGH. When lypholized and kept at 4° C. or lower, the protein was quite stable, although after a few months of storage low molecular weight products could be detected even in the absence of mercaptoethanol. Thus the material used in this study consisted of the main 20K band (~80%) and few low molecular wight bands (~20%). However, the molecule exhibited a marked degree of instability upon storage in neutral solutions with rapid accumulation of breakdown products. Met$^{14}$hGH was tested for immunological cross-reactivity with rabbit anti-hGH. It was found to be capable of displacing the [$^{125}$I]-hGH but the displacement curve did not parallel that of hGH, indicating only partial cross-reactivity.

Nb2 lymphoma cells culture

Suspension cultures of Nb2 lymphoma cells (Nb2-11C) were maintained in 75 cm$^2$ tissue culture flasks (Nunc, Kamstrup, Denmark). Culture conditions were those described by Gout, et al. (5). To stimulate maximal cell growth, cells were cultured in Fischer's medium (for leukemic mouse cells) containing FCS (10%) HS (10%), 2-mercaptoethanol (10$^{-4}$M), penicillin (50 U/ml) and streptomycin 50 $\mu$g/ml), which produced a doubling time of approximately 20 h. Stationary cultures were obtained by removing FCS from the medium 20–24 hr prior to the addition of the hormone. An incubation atmosphere of 5% CO$_2$-95% are used for cell culture. Growth of Nb2 cells was quantified according to the bioassay of Tanaka, et al. (6) with minor modifications. Growing cells were transferred to a non-growth medium (i.e. without FCS) for 20–24 h. Cells were collected by centrifugation (500$\times$g) and resuspended or directly diluted in a fresh medium (without FCS) at a concentration of 1–2 $\times$10$^5$ cells/ml. Two ml aliquots were pipetted into 35 mm tissue cultures dishes (Nunc, Kamstrup, Denmark). Samples to be assayed for growth-promoting or inhibiting activity were added to the dishes in a volume of 0.05–0.10 ml. Following a 3-day incubation period, the contents of each dish were added to 8 ml Isoton (Fisher Scientific Co., Pittsburgh, PA) and cell number was determined using a Coulter Counter (Coulter Electronics Inc., Hialeah, FL). Each sample was assayed in duplicate.

Bovine lactating mammary gland explants culture

Preparation of explants from bovine lactating mammary tissue was carried out as described previously and the media were changed every 24 h (11). Fat synthesis was determined by measuring incorporation of CH$_3$[$^{14}$]COOH to the fatty acid fraction for 4 h, after 4 days of culture and a selected hormonal regime (4). Glucose uptake was determined by measuring the glucose content of the medium prior to and after incubation.

Binding experiments

Binding studies were performed using [$^{125}$I]-hGH in intact Nb2 cells (12) or microsomal solubilized fraction prepared from lactating bovine mammary gland (9). The non-specific binding was determined in the presence of 1 $\mu$g/ml and 4 $\mu$g/ml of hGH respectively.

Statistical analysis

Statistical analyses were performed by a two-tailed Student's t test for unpaired comparisons. All parametric data were exposed as an average $\pm$SEM.

Results

Antagonistic effect of Met$^{14}$hGH on oPRL or hGH stimulated proliferation of Nb2 cells Simultaneous addition of Met$^{14}$hGH and either oPRL or hGH resulted in an obvious inhibition of the proliferation rate as compared to controls without Met$^{14}$hGH. The inhibition was dose-dependent and competitive, that is, it could be reduced by increased levels of oPRL or hGH, while the maximal proliferation rate was not affected. The inhibition could be totally abolished by increasing the concentration of the agonist (Table 1). Met$^{14}$hGH alone had no effect on cell growth and the number of cells in cultures containing 1–10000 ng/ml of Met$^{14}$hGH did not differ significantly from controls without any hormones. In an additional experiment, the cells were preincubated for 24 h in the presence of 20 $\mu$g/ml of Met$^{14}$hGH. Then they were washed extensively and incubated for an additional 3 days in the presence of 0.125 and 1.0 ng hGH/ml. The increase in cell numbers was measured every day and no difference in the proliferation rate, as compared to cells preincubated in medium only, was observed. In all experiments, the inclusion of Met$^{14}$hGH in the medium did not affect cell shape or viability as observed microscopically.

TABLE 1

Effect of excess hGH or oPRL on the growth inhibition of Nb2 lymphoma cells by Met$^{14}$hGH

| Hormone added | ng/ml | No. of doublings in presence of Met$^{14}$hGH (µg/ml): * | | |
|---|---|---|---|---|
| | | None | 2 | 10 |
| hGH | 100 | 2.25 ± 0.01 | 2.29 ± 0.01 | 2.31 ± 0.02 |
| | 25 | 2.29 ± 0.02 | 2.29 ± 0.01 | 2.30 ± 0.01 |
| | 1 | 2.20 ± 0.02 | 1.91 ± 0.01§ | 0.97 ± 0.02§ |
| oPRL | 200 | 2.22 ± 0.01 | 2.23 ± 0.02 | 2.21 ± 0.01 |
| | 20 | 2.22 ± 0.02 | 2.24 ± 0.01 | 2.09 ± 0.02§ |
| | 2 | 2.20 ± 0.01 | 2.06 ± 0.03 | 1.22 ± 0.01§ |

*Through 68 h, initial concentration of cells was 150000 cell/ml
av ± SEM, n = 2
± Significantly different from the control without Met$^{14}$hGH. ($p < 0.01$).
§as above ($p < 0.001$).

In order to validate the similarity of Met$^{14}$hGH to the native hormone, growth of Nb2 cells was stimulated by oPRL and inhibited by addition of Met$^{14}$hGH. Then the inhibitory effect of the latter was abolished by monoclonal antibodies against hGH. As shown in Table 2, the abolition was dose dependent and specific since ascitic fluid containing anti-hIgE antibodies failed to affect the response. It should be noted that two other anti-hGH monoclonal antibodies also abolished the inhibitory activity of Met$^{14}$hGH while anti-hPRL monoclonal antibody was devoid of this effect.

Inhibition of PRL stimulated fat synthesis in explants from bovine lactating mammary glands by Met$^{14}$hGH The results presented in Table 3 clearly indicate that bPRL-stimulated fat synthesis was drastically inhibited in explants cultured in the presence of 10-50 µg/ml Met$^{14}$hGH/ml. Moreover, in explants from Cows no. 1 and 4, Met$^{14}$hGH also significantly inhibited fat synthesis in the absence of bPRL. Analysis of the data again suggested competitive inhibition although it was less obvious than in the experiments using Nb2 cells. Glucose uptake, which served as an index of explant viability (4) was not affected by various hormonal regimes including addition of Met$^{14}$hGH. It should be noted that in the absence of Met$^{14}$hGH addition of bPRL significantly ($p < 0.05$) increased fat synthesis, although in explants from some cows (2, 3 and 5) the maximal effect was not reached at 0.2 µg PRL/ml.

Binding studies

Binding studies with intact Nb2 cells or with solubilized microsomal fraction from bovine lactating mammary gland revealed Met$^{14}$hGH to be capable of inhibiting the specific binding of $^{125}$I-hGH in both cases.

TABLE 2

Effect of monoclonal antibodies against hGH on the growth of oPRL-stimulated Nb2 lymphoma cells by Met$^{14}$hGH

| Antibody* added | Final* dilution | No. of doublings in presence of oPRL (ng/ml):+ | | | |
|---|---|---|---|---|---|
| | | 1.000 | | 0.125 | |
| | | −Met$^{14}$hGH | +Met$^{14}$hGH | −Met$^{14}$hGH | +Met$^{14}$hGH |
| None | — | 2.13 ± 0.01 | 1.23 ± 0.04 | 1.14 ± 0.03 | 0.42 + 0.05 |
| anti-hIge | 1:100 | 2.11 ± 0.02 | 1.23 ± 0.01 | 1.16 ± 0.03 | 0.44 ± 0.02 |
| anti-hGH | 1:100 | 2.11 ± 0.02 | 2.09 ± 0.06 | 1.19 + 0.03 | 1.14 ± 0.01 |
| anti-hGH | 1:400 | 2.10 ± 0.02 | 1.92 ± 0.03 | 1.14 ± 0.01 | 0.98 ± 0.03 |
| anti-hGH | 1:1600 | 2.11 ± 0.01 | 1.68 ± 0.01 | 1.11 ± 0.02 | 0.62 ± 0.02 |
| anti-hGH | 1:6400 | 2.10 ± 0.02 | 1.46 + 0.01 | 1.12 ± 0.01 | 0.51 ± 0.02 |

*Ascitic fluids
+av ± SEM, n = 2, through 66 h.
12 µg/ml
Significantly different from the respective control without Met$^{14}$hGH ($p < 0.001$).

TABLE 3

Effect of various concentrations of bPRL on the inhibition of the bPRL stimulated fatty acid synthesis by Met$^{14}$hGH in explants from bovine lactating mammary gland

| Cow no. | Met$^{14}$hGH (µg/ml) | Fatty acid synthesis (dpm/mg/4 h) in the presence of various concentrations of bPRL (µg/ml):*+ | | | | |
|---|---|---|---|---|---|---|
| | | 0 | 0.2 | 1.0 | 2.0 | 20.0 |
| 1 | 0 | 3814 ± 89 | 5064 ± 326 | 5809 ± 393 | ND | ND |
| | 10 | ND | 3220 ± 93 | 4812 ± 258 | ND | ND |
| | 50 | 3212 ± 88 | 3257 ± 259 | 2682 ± 119 | ND | ND |
| 2 | 0 | 476 ± 55 | 859 ± 47 | 1033 ± 57 | ND | ND |
| | 10 | ND | 549 ± 47 | 598 ± 39 | ND | ND |
| | 50 | 486 ± 45 | 525 ± 29 | 525 ± 57 | ND | ND |
| 3 | 0 | 822 ± 35 | 1496 ± 366 | ND | ND | 2080 ± 322 |
| | 20 | 793 ± 80 | 1061 ± 61 | ND | ND | 1300 ± 181 |
| 4 | 0 | 2046 ± 241 | 2981 ± 124 | ND | 2979 ± 236 | 2280 ± 258 |
| | 20 | 1088 ± 148 | 1126 ± 61 | ND | 1496 ± 175 | 1696 ± 186 |
| 5 | 0 | 449 ± 37 | 735 ± 50 | ND | 1150 ± 118 | 1048 ± 88 |
| | 1 | 441 ± 21 | 778 ± 56 | ND | 896 ± 50 | 881 ± 80 |
| | 2.5 | 514 ± 12 | 612 ± 60 | ND | 994 ± 57 | 724 ± 47 |
| | 10 | 430 ± 12 | 431 ± 45 | ND | 743 ± 56 | 645 ± 58 |

*All treatments included insulin (1 µg/ml) and hydrocortisone (0.5 µg/ml)
+av ± SEM, n = 6
Significantly different from the respective treatment without Met hGH: ($p < 0.05$)
as above ($p < 0.01$)
as above ($p < 0.0001$)

Full or almost full displacement of the ligand could be achieved but the amounts of Met$^{14}$hGH required for 50% of displacement were respectively 83- and 35-fold higher than those of hGH.

Discussion

Utilization of two separate bioassay systems enabled us to demonstrate clearly that the recombinant Met$^{14}$hGH inhibits hGH- and oPRL-stimulated mitogenesis of Nb2 lymphoma cells and bPRL-stimulated fat synthesis in explants of bovine lactating mammary gland. In the latter system Met$^{14}$hGH also inhibited (cows no. 3-5) bPRL stimulated secretion of α-lactalbumin (not shown), thus implying more general inhibition of prolactic action. It should be noted that in both systems the inhibition did not result from impaired cell viability. No cytotoxic effect was found in Nb2 cells exposed to Met$^{14}$hGH. Glucose uptake in mammary gland explants was not affected by various treatments. It should be noted that in cows no. 1 and 4 Met$^{14}$hGH also inhibited basal activity. The reason for this is not clear but may be related to a much higher intrinsic fat synthesis in these cows. Whether the latter results from carryover of endogenous prolactic or PRL-stimulated activity is not clear.

Binding experiments revealed that Met$^{14}$hGH competes with $^{125}$I-hGH although its affinity is lower than that of hGH. These results imply that Met$^{14}$hGH may act as an antagonist, namely blocking the agonist at the receptor or post-receptor level. The maximal rate of proliferation was not changed by the inhibitor but the apparent affinity of either oPRL or hGH was decreased. Although the biological significance of this constant is not clear since it is a function of both binding and post-binding events its value in the absence of Met$^{14}$hGH (3.85 pM for hGH and 2.95 pM for oPRL) is close to the value of 5.8 pM of $^{125}$I-hPRL required for half-maximal growth of the cells (7). It was found that in order to achieve 50% growth inhibition $10^3$–$10^4$ molar excess of Met$^{14}$hGH were needed, despite the fact that the affinity to bind to intact cells in only ~85 fold lower. This may be related to the finding that full growth response may be achieved at 35% receptor occupancy (7).

Unlike in Nb2 cells, the competitive inhibition of bPRL stimulated fat synthesis in explants is much less obvious. A trend showing this direction was seen in cow number 1 where the inhibition with 10 μg/ml of Met$^{14}$gGH was significantly lower at 0.2 μg/ml, than at 1.0 μg/ml, and to a lesser degree in cow numbers 2, 4 and 5. In the latter case, 10 μg/ml of Met$^{14}$hGH absolutely abolished PRL stimulation at the 0.2 μg/ml, while at 2 and 20 μg bPRL/ml there was only partial inhibition. It should be remembered that the explants consist of primary cultures that are much more variable to the absolute and relative hormonal stimulation than the Nb2 cells. The explant system seems also to be more sensitive, and significant inhibition was achieved in 0.5-50 Met$^{14}$hGH/bPRL molar ratios. Although the apparent affinity constant for the binding of hGH to the mammary gland receptors is 20-35 fold higher than for Met$^{14}$hGH we have previously demonstrated (9) that it is also 20-fold higher than for bPRL thus making the binding constant of the latter and the Met$^{14}$hGH quite comparable.

The finding that the preparation of Met$^{14}$hGH used in this investigation also contained some low molecular weight degradation products raises a possibility that they, rather than the main 20K band, may be responsible for the inhibitory effect. The fact that monoclonal antibodies against hGH abolished the inhibitory activity of Met$^{14}$hGH argues against this suggestion. In addition, we have purified small amounts of Met$^{14}$hGH by immunoaffinity chromatography on anti-hGH monoclonal antibody coupled to Sepharose. The purified material gave a single 20K band on NaDodSO$_4$/polyacrylamide gel electrophoresis and retained its full inhibitory activity against oPRL-stimulated proliferation of Nb2 cells (data not shown).

To our knowledge this is the first report describing inhibition of hGH activity by a modified hGH. Careful examination of the data compiled by Paladini, et al. (13) reveals that removal of the N-terminal portion of hGH drastically reduced and in most cases absolutely abolished its lactogenic or somatotrophic activity. The importance of the N-terminal part of oPRL for its in vivo mitogenic activity also has been reported (14). In view of these results and our present findings it seems that the N-terminal part of these hormones is obligatory for expression of activity. Its removal may cause inactivation or even conversion of an agonist to antagonist. It should also be remembered that in both systems used in our experiments the hormonal effect was mediated through lactogenic receptors. Whether similar inhibitory effect of Met$^{14}$hGH can be found in somatotrophic receptor-mediated activity has yet to be investigated.

REFERENCES

1. Chadwick, S., Folley, S. J., & Forsyth, I. A. (1961) *Lancet*, 2, 241-243.
2. Doneen, B. (1976) *Gen. Comp. Endocrinol.*, 34, 34-42.
3. Kleinberg, D. L. & Todd, J. (1980) *J. Clin. Endocrinol. Met.* 51, 1009-1013.
4. Gertler, A., Cohen, N. & Maoz, A. (1983) *Mol. Cell. Endocrinol.*, 33, 169-182.
5. Gout, P. W., Beer, C. T. & Nobel, P. R. (1980) *Cancer Res.*, 40, 2433-2446.
6. Tanaka, T., Shieu, R. P. C., Gout, P. W., Beer, C. T., Noble, R. L. & Friesen, H. G. (1980) *J. Clin. Endocrinol. Met.*, 51, 1058-1063.
7. Shiu, R. P. C., Elsholtz, H. P., Tanaka, T., Friesen, H. G., Gout, P. W., Beer, C. T. & Noble, R. L. (1983) *Endocrinology*, 113, 159-165.
8. Shiu, R. P. C., (1979) *Cancer Res.*, 39, 4381-4386.
9. Gertler, A., Ashkenazi, A. & Madar, Z. (1984) *Mol. Cell. Endocrinol*, 34, 51-57.
10. Bundeson, P., Drake, R. G., Kelly, K., Worsley, I. G., Friesen, H. G. & Sehon, A. (1981) *J. Clin Endocrinol Met.*, 51, 1472-1474.
11. Gertler, A., Weil, A. & Cohen, N. (1982) *J. Dairy Res.*, 49, 387-398.
12. Gertler, A., Walker, A. & Friesen, H. G. (1985) *Endocrinology* (in press).
13. Paladini, A. C., Pena, C. & Poskus, E. (1983) *CRC, Critical Reviews in Biochemistry*, 15, 1-56. 14. Mittra, I. (1980) *Biochem. Biophys. Res. Commun.*, 95, 1760-1767.

What is claimed is:

1. A polypeptide which inhibits the activity of naturally-occurring human growth hormone (hGH) or naturally-occurring prolactin (PRL), said polypeptide having the sequence of naturally-occurring hGH from what the first thirteen amino acids have been deleted and which has the methionine which occurs at position 14 of the naturally-occurring polypeptide at the N-terminus.

2. A pharmaceutical composition comprising an effective amount of the polypeptide of claim 1 and a suitable carrier.

3. A method of treating human growth hormone (hGH) excess or prolactin (PRL) excess which comprises administering to a subject having such an excess an effective amount of the polypeptide of claim 1.

* * * * *